(12) United States Patent
Damon et al.

(10) Patent No.: US 6,313,142 B1
(45) Date of Patent: Nov. 6, 2001

(54) METHOD FOR MAKING 4-CARBOXYAMINO-2-SUBSTITUTED-1,2,3,4-TETRAHYDROQUINOLINE

(75) Inventors: David B. Damon, Mystic; Robert W. Dugger, Stonington, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/684,830

(22) Filed: Oct. 10, 2000

Related U.S. Application Data

(60) Provisional application No. 60/167,967, filed on Nov. 30, 1999.

(51) Int. Cl.[7] .......................... A61K 31/47; C07D 215/38
(52) U.S. Cl. ............................................. 514/313; 546/159
(58) Field of Search ................................ 546/159; 514/313

(56) References Cited

U.S. PATENT DOCUMENTS

| | | |
|---|---|---|
| 3,971,789 | 7/1976 | Archibald et al. . |
| 4,695,574 | 9/1987 | Boyle et al. . |
| 5,231,102 | 7/1993 | Baker et al. . |

FOREIGN PATENT DOCUMENTS

| | | | |
|---|---|---|---|
| 0243982 | 4/1987 | (EP) . | |
| 0987251 | 3/2000 | (EP) . | |
| 0992496 | 4/2000 | (EP) . | |
| WO 8908104 | 10/1989 | (WO) . | |
| WO0017164 | 3/2000 | (WO) | ........................... 546/159 |

OTHER PUBLICATIONS

Gordon, D.J., et al.,: "High–density Lipoprotein Cholesterol and Cardiovascular Disease", Circulation, (1989), 79: 8–15.

*Primary Examiner*—Alan L. Rotman
*Assistant Examiner*—Raymond Covington
(74) *Attorney, Agent, or Firm*—Peter C. Richardson; Gregg C. Benson; Arlene K. Musser

(57) ABSTRACT

Methods of preparing CETP inhibitors are disclosed.

18 Claims, No Drawings

METHOD FOR MAKING 4-CARBOXYAMINO-2-SUBSTITUTED-1,2,3,4-TETRAHYDROQUINOLINE

BACKGROUND OF THE INVENTION

This application claims priority from provision application U.S. Ser. No. 60/167,967, filed Nov. 30, 1999, the benefit of which is hereby claimed under 37 C.F.R.§1.78(a)(3).

This invention relates to cholesteryl ester transfer protein (CETP) inhibitors, and method for making such inhibitors.

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of this condition has been shown to be strongly correlated with certain plasma lipid levels. While elevated LDL-cholesterol may be the most recognized form of dyslipidemia, it is by no means the only significant lipid associated contributor to CHD. Low HDL-C is also a known risk factor for CHD (Gordon, D.J., et al.,: "High-density Lipoprotein Cholesterol and Cardiovascular Disease", Circulation, (1989), 79: 8–15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL-C only modestly. As a result, there is a significant unmet medical need for a well-tolerated agent which can significantly elevate plasma HDL levels, thereby reversing or slowing the progression of atherosclerosis.

Commonly assigned U.S. application Ser. No. 09/391,152 filed Sep. 7, 1999 entitled 4-CARBOXYAMINO-2-SUBSTITUTED-1,2,3,4-TETRAHYDROQUINOLINES, the disclosure of which is hereby incorporated by reference, is directed to compounds of the following general formula:

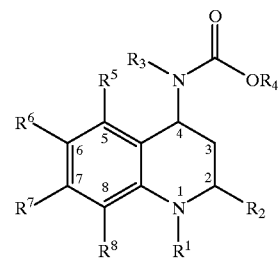

Specifically, the compound [2R,4S]4-[(3,5bis-trifluoromethyl-benzyl)-methoxycarbonyl-amino]-2-ethyl-6-trifluoromethyl-3,4-dihydro-2H-quinoline-1-carboxylic acid ethyl ester is described. A process for making this compound is also described in Example 7.

Thus, although there are a variety of anti-atherosclerosis therapies, there is a continuing need and a continuing search in this field of art for compounds for the treatment of atherosclerosis, and accordingly methods for making such compounds.

SUMMARY OF THE INVENTION

One aspect of this invention is 4-(3,5bis-trifluoromethylbenzylamino)-2-ethyl-6-trifluoromethyl-3,4-dihydro-2H-quinoline-1-carboxyl add ethyl ester, 4-toluene-sulfonate.

Another aspect of this invention is (−)-(2R,4S)-4-(3,5-bis-trifluoromethylbenzylamino)-2-ethyl-6-trifluoromethyl-3,4-dihydro-2H-quinoline-1-carboxyl acid ethyl ester or pharmaceutically acceptable salts thereof, preferably the 4-toluene-sulfonate salt thereof.

Another aspect of this invention is cis-4-amino-2-ethyl-6-trifluoromethyl-3,4-dihydro-2H-quinoline-1-carboxylic acid ethyl ester and pharmaceutically acceptable salts thereof, preferably the (−)di-benzoyl-L-tartrate salt or (−)di-p-toluoyl-L-tartaric acid salt thereof.

Another aspect of this invention is (−)(2R,4S)-4-amino-2-ethyl-6-trifluoromethyl-3,4-dihydro-2H-quinoline-1-carboxylic acid ethyl ester and pharmaceutically acceptable salts thereof, preferably the (−)di-benzoyl-L-tartrate salt or (−)di-p-toluoyl-L-tartaric acid salt thereof.

Another aspect of this invention is directed to a process for preparing (−)-(2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprising combining (−)-(2R,4S)-4-(3,5-bis-trifluoromethyl-benzylamino)-2-ethyl-6-trifluoromethyl-3,4-dihydro-2H-quinoline-1-carboxylic acid ethyl ester, 4-toluene-sulfonate and sodium carbonate in tetrahydrofuran at a temperature of about 20° C. to about 25° C. in the presence of methyl chloroformate.

Another aspect of this invention is directed to a process for preparing (−)-(2R,4S)-4-(3,5-bis-trifluoromethyl-benzylamino)-2-ethyl-6-trifluoromethyl-3,4-dihydro-2H-quinoline-1-carboxylic acid ethyl ester, 4-toluene-sulfonate comprising a. combining 4-amino-2-ethyl-6-trifluoromethyl-3,4-dihydro-2H-quinoline-1-carboxylic acid ethyl ester and (−) dibenzoyl-L-tartaric acid (anhydrous) or (−)di-p-toluoyl-L-tartaric acid to form the (−) dibenzoyl-L-tartaric acid salt or di-p-toluoyl-L-tartaric acid salt thereof;

b. combining the resulting salt, 1,2-dichloroethane and an aqueous base with 3,5-bis(trifluoromethyl) benzaldehyde, followed by the addition of sodium triacetoxyborohydride; and c. adding 4-toluene sulfonic acid monohydrate.

Preferably the (−) dibenzoyl-L-tartaric acid (anhydrous) is used.

Another aspect of this invention is directed to a process for preparing 4-amino-2-ethyl-6-trifluoromethyl-3,4-dihydro-2H-quinoline-1-carboxylic acid ethyl ester comprising; combining cis-4-benzyloxycarbonylamino-2-ethyl-6-trifluoromethyl-3,4dihydro-2H-quinoline-1-carboxylic acid ethyl ester and ammonium formate in methanol with palladium/carbon to form a slurry and heating the resulting slurry at a temperature of about 35° C. to about 60° C. for about 30 minutes to about 3 hours.

Another aspect of this invention is directed to a process for preparing cis-(2-ethyl-6-trifluoromethyl-1,2,3,4-tetrahydro-quinolin4-yl)-carbamic acid-$R^1$-ester, wherein $R^1$ is benzyl,t-butyl or $C_1$–$C_4$(alkyl), comprising: combining vinyl-carbamic acid-$R^1$, (1-benzotriazol-1-yl-propyl)-(4-trifluoromethyl-phenyl)-amine and 4-toluene-sulfonic acid monohydrate in toluene at a temperature of about 50° C. to about 90° C. Preferably the process includes the additional step of combining the resulting cis-(2-ethyl-6-trifluoromethyl-1,2,3,4-tetrahydro-quinolin-4-yl)-carbamic acid-$R^1$-ester with pyridine and ethyl choroformate in dichloromethane to prepare cis-4-$R^1$-oxycarbonylamino-2-ethyl-6-trifluoromethyl-3,4-dihydro-2H-quinoline-1-carboxylic acid ethyl ester.

Another aspect of this invention is directed to a process for preparing (−)-(2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprising a. combining vinyl-carbamic acid-$R^1$, wherein $R^1$ is benzyl, (1-benzotriazol-1-yl-propyl)-(4-trifluoromethyl-phenyl)-amine and 4-toluene-sulfonic acid monohydrate in toluene at a temperature of about 50° C. to about 90° C. to prepare cis-(2-ethyl-6trifluoromethyl-1,2,3,4-tetrahydro-quinolin-4-yl)-carbamic acid-$R^1$-ester wherein $R^1$ is benzyl;

b. combining the resulting cis-(2-ethyl-6-trifluoromethyl-1,2,3,4-tetrahydro-quinolin-4-yl)-carbamic acid-$R^1$-ester with pyridine and ethyl choroformate in dichloromethane to prepare cis-4-$R^1$-oxycarbonylamino-2-ethyl-6-trifluoromethyl-3,4-dihydro-2H-quinoline-1-carboxylic acid ethyl ester;

c. combining cis-4-$R^1$-oxycarbonylamino-2-ethyl-6-trifluoromethyl-3,4-dihydro-2H-quinoline-1-carboxylic acid ethyl ester and ammonium formate in methanol with palladium/carbon to form a slurry and heating the resulting slurry at a temperature of about 35° C. to about 60° C. for about 30 minutes to about 3 hours to prepare 4-amino-2-ethyl-6-trifluoromethyl-3,4-dihydro-2H-quinoline-1-carboxylic acid ethyl ester;

d. combining 4-amino-2-ethyl-6-trifluoromethyl-3,4-dihydro-2H-quinoline-1-carboxylic acid ethyl ester and (−)dibenzoyl-L-tartaric acid or (−)di-p-toluoyl-L-tartaric acid to form the (−)dibenzoyl-L-tartaric acid salt or di-p-toluoyl-L-tartaric acid salt thereof;

e. combining the resulting salt, 1,2-dichloroethane and an aqueous base with 3,5-bis(trifluoromethyl) benzaldehyde, followed by the addition of sodium triacetoxyborohydride to form a product;

f. combining said product and 4-toluene sulfonic acid monohydrate to prepare (−)-(2R,4S)-4-(3,5-bis-trifluoromethyl-benzylamino)-2-ethyl-6-trifluoromethyl-3,4-dihydro-2H-quinoline-1-carboxylic acid ethyl ester, 4-toluene-sulfonate; and g. combining (−)-(2R,4S)-4-(3,5-bis-trrifluoromethyl-benzylamino)-2-ethyl-6-trifluoromethyl-3,4-dihydro-2H-quinoline-1-carboxylic acid ethyl ester, tosylate salt, methyl chloroformate and sodium carbonate in tetrahydrofuran at a temperature of about 20° C. to about 25° C. in the presence of methyl chloroformate.

In contrast to the process described in Example 7 of U.S. application Ser. No. 09/391,152, the four intermediates II, V, VI and VII are easily isolated and purified as crystalline material. The formation of III produces a purer product since the reaction is performed with pure starting material II. The resolution via a classical diastereomeric salt formation is much easier to scale than the use of chiral chromatography. Further crystallization of final products (e.g., the anhydrous form, the ethanolate form) is facilitated by the high purity of the formula VII compound.

As used herein the term mammals is meant to refer to all mammals which contain CETP in their plasma, for example, rabbits and primates such as monkeys and humans. Certain other mammals e.g., dogs, cats, cattle, goats, sheep and horses do not contain CETP in their plasma and so are not included herein.

The term ethanolate refers to an ethanol of solvation.

By "pharmaceutically acceptable" it is meant the carrier, vehicle, diluent, excipients, and/or salt must be compatible with the other ingredients of the formulation, and not deleterious to the recipient thereof.

As used herein, the expressions "reaction-inert solvent" and "inert solvent" refers to a solvent or mixture of solvents which does not interact with starting materials, reagents, intermediates or products in a manner which adversely affects the yield of the desired product.

Other features and advantages will be apparent from the specification and claims which describe the invention.

DETAILED DESCRIPTION OF THE INVENTION

In general the compound of this invention, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, can be made by processes which include analogous processes known in the chemical arts, particularly in light of the description contained herein. Certain processes for the manufacture of the compound of this invention are provided as further features of the invention and are described below including in the experimental section.

SCHEME

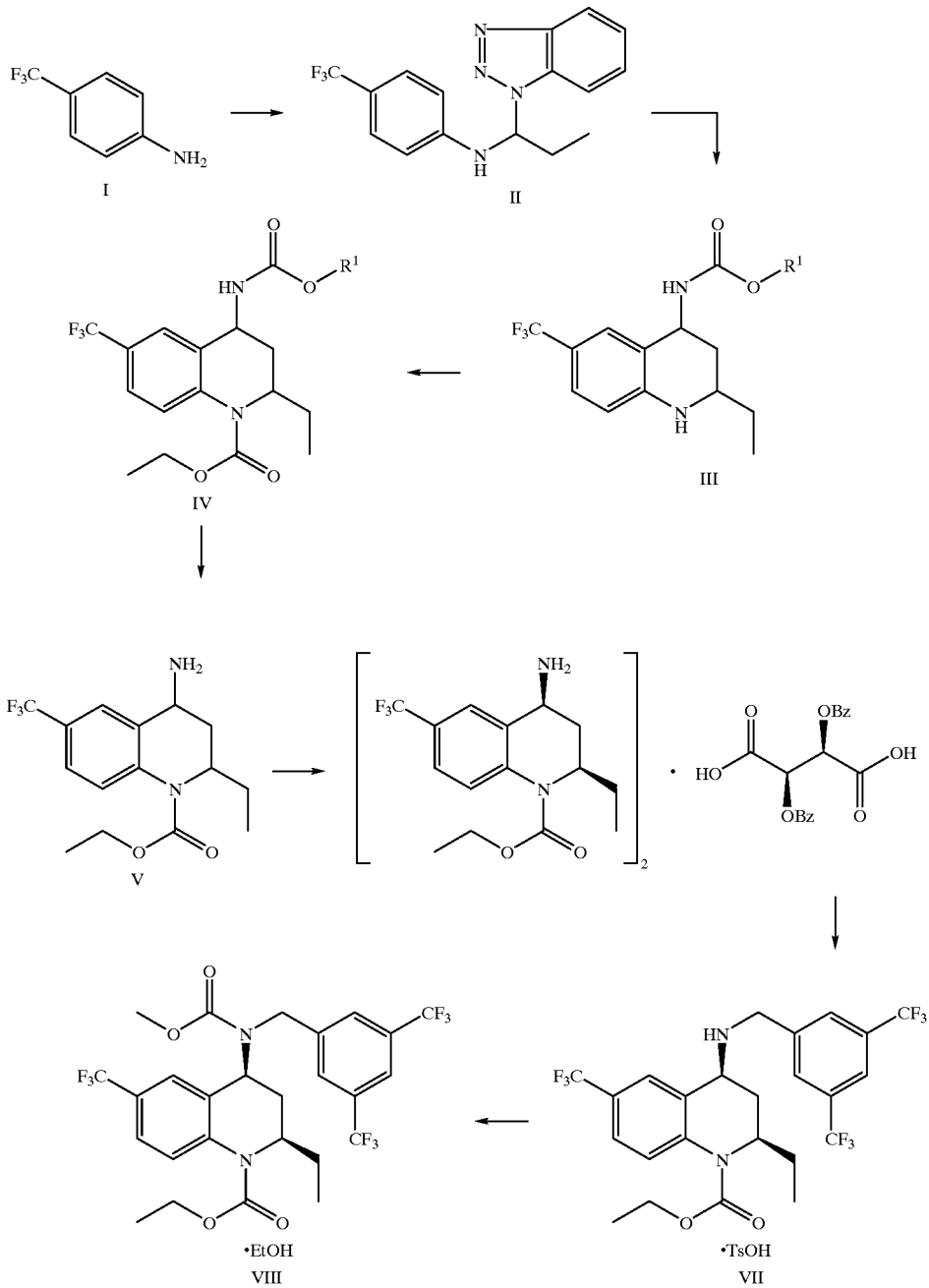

According to the above Scheme, the formula II amine may be prepared by combining benzotriazole, 4(trifluoromethyl)aniline (I) and propionaldehyde in a nonpolar solvent such as toluene at ambient temperature (about 20° C. to about 30° C. for about 0.5 to about 3 hours.

The formula III ester may be prepared by combining vinyl-carbamic acid $R^1$ ester (wherein $R^1$ is benzyl, t-butyl or $(C_1-C_4)$alkyl), the formula II amine and p-toluenesulfonic acid monohydrate in an inert solvent such as toluene at elevated temperature (about 50° C. to about 90° C.) for about 0.5 to about 3 hours. Preferably, $R^1$ is benzyl.

The formula IV compound may be prepared by combining the formula III ester, ethyl chloroformate and an amine base such as pyridine in an inert, nonnucleophilic solvent such as dry dichloromethane resulting in an exothermic reaction.

The formula V compound may be prepared by treating the product of the preceding reaction with ammonium formate, palladium on carbon in a polar, protic solvent such as methanol at a temperature of about 35° C. to about 60° C. for about 0.5 hour to about 3 hours.

The reaction sequence proceeds via preparation of a classical diastereomeric salt formation by combining 4-amino-2-ethyl-6-trifluoromethyl-3,4-dihydro-2H- quinoline-1-carboxylic acid ethyl ester and (−) dibenzoyl-L-tartaric acid (anhydrous) followed by the addition of an alcoholic solvent such as ethanol at a temperature of ambient (e.g., about 20° C. to about 30° C.) for about 1 to about 24 hours to form the (−)dibenzoyl-L-tartaric acid salt thereof. Alternatively, (−) di-p-toluoyl-L-tartaric acid may be used in place of the (−)dibenzoyl-L-tartaric acid.

The formula VII compound may be prepared by treating the formula VI salt, 1,2-dichloroethane and an aqueous base such as sodium hydroxide with 3,5-bis(trifluoromethyl) benzaldehyde followed by the addition of sodium triacetoxyborohydride at ambient temperature (e.g., about 20° C. to about 30° C.) for about 1 hour to about 24 hours. Subsequently 4-toluenesulfonic acid monohydrate is added at ambient temperature (e.g., about 20° C. to about 30° C.).

The formula VIII compound may be prepared by combining (−)-(2R,4S)-4-(3,5-bis-trifluoromethyl-benzylamino)-2-ethyl-6-trifluoromethyl-3,4-dihydro-2H-quinoline-1-carboxylic acid ethyl ester and sodium carbonate in tetrahydrofuran at ambient temperature (e.g., about 20° C. to about 25° C.) in the presence of methyl chloroformate. An ethanolate crystalline form of the above compound may be prepared from the amorphous compound by recrystallization from ethanol/water at a temperature of about 20° C. to about 25° C., preferably ambient temperature for about 0.5 hour to about 18 hours. Typically the range is about 3% to about 10% ethanol and about 90% to about 97% water. Preferably the ratio is about 10% to about 90% ethanol/water.

Alternatively, the ethanolate crystalline form may be prepared utilizing procedures analogous to those described above but using ethanol alone. The filtered materials are typically granulated for about 2 hours to about 24 hours followed by air drying.

The amorphous form of the compound [2R,4S]4-[(3,5-bis-trifluoromethyl -benzyl)-methoxycarbonyl-amino]-2-ethyl-6-trifluoromethyl-3,4-dihydro-2H-quinoline-1-carboxylic acid ethyl ester is prepared as described in Example 10 herein below.

An anhydrous crystalline form of the above compound may be prepared from the amorphous compound by recrystallization from hexanes (solvent comprised of hexane isomers (e.g., n-hexane, cyclohexane, methyl pentane, etc.)) at a temperature of about 40° C. to about 80° C., preferably 60° followed typically by granulating the filtered material for about 2 to about 24 hours and subsequent air drying.

Alternatively, the anhydrous crystal may be prepared from the ethanolate crystalline form (described below) utilizing analogous procedures to the immediately preceding procedure. In addition, the yield in this procedure may be enhanced by azeotroping the ethanol from the hexanes.

It is noted that as the anhydrous and ethanolate crystals are of different energy levels seeding with either anhydrous or ethanolate may determine the resulting isolated crystalline form. As is known in the art the presence of seed crystals in the air in a lab may be sufficient "seeding." In one embodiment anhydrous crystals may be obtained using hexanes and the resulting anhydrous crystals may be used to seed the production of further anhydrous crystals from ethanol.

A preferred dosage is about 0.1 to 100 mg/kg/day of the compound prepared by the process of this invention, preferably the anhydrous crystals. An especially preferred dosage is about 0.1 to 10 mg/kg/day.

The compound of this invention may be used for the treatment of atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal (including a human being either male or female).

The compound of this invention may also be used in combination with a second compound. The second compound may be an HMG-CoA reductase inhibitor, a microsomal triglyceride transfer protein (MTP)/Apo B secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

The dosage of the compound of the instant invention which is administered will generally be varied according to principles well known in the art taking into account the severity of the condition being treated and the route of administration. In general, the compound will be administered to a warm blooded animal (such as a human, livestock or pet) so that an effective dose, usually a daily dose administered in unitary or divided portions, is received, for example a dose in the range of about 0.01 to about 100 mg/kg/day body weight, preferably about 0.1 to about 10 mg/kg/day body weight. The above dosages are exemplary of the average case; there can, of course, be individual instances where higher or lower doasge ranges are merited, and such deviations are within the scope of this invention.

The compound of the instant invention is orally administrable and is accordingly used in combination with a pharmaceutically acceptable carrier, vehicle or diluent suitable to oral dosage forms. Suitable pharmaceutically-acceptable carriers include inert solid fillers or diluents and sterile aqueous or organic solutions. The active compound will be present in such pharmaceutical compositions in amounts sufficient to provide the desired dosage amount in the range described herein. Thus, for oral administration the compound may be combined with a suitable solid or liquid carrier, vehicle or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, for example a gel capsule, it may contain, in addition to or instead of materials of the above type, a liquid carrier such as a fatty glyceride or mixtures of fatty glycerides, such as olive oil, or Migloyl™ or Capmul™ glycerides.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compound of the instant invention may also be administered parenterally. For parenteral administration the compound may be combined with sterile aqueous or organic media to form injectable solutions or suspensions. The injectable solutions prepared in this manner can then be administered intravenously, intraperitoneally, subcutaneously, or intramuscularly.

The pharmaceutical forms suitable for injectable use include sterile solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. They may be sterilized, for example, by filtration through a bacteria-retaining filter, by incorporating sterilizing agents into the compositions, or by irradiating or heating the compositions where such irradiating or heating is both appropriate and compatible with the drug formulation.

Additional pharmaceutical formulations may include, inter alia, suppositories, sublingual tablets, topical dosage forms and the like and these may be prepared according to methods which are commonly accepted in the art.

EXAMPLES

Melting points were determined with a Thomas Hoover melting point apparatus or a DSC apparatus. Unless otherwise stated, $CDCl_3$ was used for NMR spectra. Microanalysis was performed by Schwarzkopf Microanalytical Laboratory. All reagents and solvents were obtained commercially and used without purification.

Example 1

(1-Benzotriazol-1-yl-propyl)-(4-trifluoromethyl-phenyl)-amine

A two liter, four neck flask under nitrogen atmosphere was charged with benzotriazole (36.96 g, 310 mmol, 1.0 equiv) and dry toluene (400 mL). A room temperature solution of 4-(trifluoromethyl)aniline (39.1 mL, 310 mmol, 1.0 equiv) and 50 mL toluene was added over one minute. A room temperature solution of propionaldehyde (24.6 mL, 341 mmol, 1.1 equiv) and 50 mL toluene was then added over 20 minutes. There was an exotherm from 23° C. to 30° C. during this addition. After stirring 24 h, n-heptane (500 mL) was added, and the slurry stirred an additional 1 h. The suspension was filtered, the solids were washed with n-heptane (1×100 mL, then 1×200 mL), and dried. (1-Benzotriazol-1-yl-propyl)-(4-trifluoromethyl-phenyl)-amine was isolated as shiny white needles (81.3 g, 82%). After 24 h, a second crop was isolated from the filtrate (8.7 g, 9%). mp 130–132° C.; $^1$H NMR (DMSO-d6, 400 MHz) δ0.82 (t, 3H, J=7.5 Hz), 2.25 (m, 2H), 6.49 (m, 1H), 6.80 (d, 2H, J=8.7 Hz), 7.35 (m, 3H), 7.50 (m, 1H), 7.88 (d, 1H, J=8.3 Hz), 7.99 (m, 1H), 8.09 (d, 1H, J=8.5 Hz); $^{13}$C NMR (DMSO-d6, 100 MHz) δ149.32, 146.19, 131.46, 127.73, 126.8, 125.33 (q, J=270 Hz), 124.44, 119.88, 118.27 (q, J=31.7 Hz), 112.91, 111.56, 71.03, 28.08, 10.29; DEPT spectrum: quaternary carbons δ149.32, 146.19, 131.46, 125.33, 118.27; CH carbons δ127.73, 126.8, 124.44, 119.88, 112.91, 111.56, 71.03; $CH_2$ carbon δ28.08; $CH_3$ carbon δ10.29; IR (drifts) 3292 (s), 3038 (m), 2975 (m), 1621 (s), 1331 (s), 1320 (s), 1114 (vs); Anal. Calcd for $C_{16}H_{15}N_4F_3$: C, 59.99; H, 4.72; N, 17.49. Found (first crop): C, 60.16; H, 4.74; N, 17.86. Found (second crop): C, 59.97; H, 4.66; N, 17.63.

Example 2 cis-(2-Ethyl-6-trifluoromethyl-1,2,3,4-tetrahydro-quinolin-4-yl)-carbamic acid benzyl ester A one liter, four neck flask under nitrogen atmosphere was charged with N-vinyl-carbamic acid benzyl ester (27.66 g, 156 mmol, 1.0 equiv) and dry toluene (500 mL). (1-Benzotriazol-1-yl-propyl)-(4-trifluoromethyl-phenyl)-amine (50.0 g, 156 mmol, 1.0 equiv) and p-toluenesulfonic acid monohydrate (297 mg, 1.56 mmol, 0.01 equiv) were added, and the mixture heated to 70° C. After 2 h, the mixture was cooled to room temperature and transferred to a separatory funnel. Ethyl acetate (500 mL) was added. The mixture was washed 1×200 mL 1 N NaOH, 1×200 mL $H_2O$, 1×200 mL brine, and dried ($MgSO_4$). The mixture was filtered and the solids washed 1×50 mL ethyl acetate. The filtrate was concentrated to approximately 250 mL. 500 mL toluene were added, and the mixture concentrated to approximately 500 mL. 500 mL n-heptane were added, the slurry was stirred 1 h, filtered through a Buchner funnel, and dried. cis-(2-Ethyl-6-trifluoromethyl-1,2,3,4-tetrahydro-quinolin4-yl)-carbamic acid benzyl ester was isolated as a white powder (45.04 g, 76%): mp 155–157° C.; $^1$H NMR (DMSO-d6, 400 MHz) δ0.92 (t, 3H, J=7.5 Hz), 1.5 (m, 3H), 2.00 (m, 1H), 3.35 (m, 1H), 4.77 (m, 1H), 5.07 (d, 1H, J=12.5 Hz), 5.15 (d, 1H, J=12.5 Hz), 6.35 (s, 1H), 6.61 (d, 1H, J=8.5 Hz), 7.12 (s, 1H), 7.18 (dd, 1H, J=1.9, 8.5 Hz), 7.4 (m, 5H), 7.70 (d, 1H, J=9.1 Hz); $^{13}$C NMR (DMSO-d6, 100 MHz) δ157.03, 149.02, 137.79, 128.82, 128.23, 128.03, 125.9 (q, J=270 Hz), 125.06, 123.50, 121.73, 115.2 (q, J=31.7 Hz), 113.33, 65.85, 52.09, 47.83, 34.02, 28.68, 9.93; DEPT spectrum: quaternary carbons δ157.03, 149.02, 137.79, 125.9, 121.73, 115.2; CH carbons δ128.82, 128.23, 128.03, 125.06, 123.50, 113.33, 52.09, 47.83; $CH_2$ carbons δ65.85, 34.02, 28.68; $CH_3$ carbon δ9.93; IR (drifts) 3430 (m), 3303 (s), 2951 (m), 1686 (vs), 1542 (vs), 1088 (vs); MS (APCI+) m/z (rel. intensity) 379 (M+H$^+$, 53), 228 (100); Anal. Calcd for $C_{20}H_{21}N_2O_2F_3$: C, 63.48; H, 5.59; N, 7.40; Found: C, 63.69; H, 6.06, N, 7.36.

Example 3 cis4-Benzyloxycarbonyiamino-2-ethyl-6-trifluoromethyl-3,4-dihydro-2H-quinoline-1-carboxylic acid ethyl ester A three liter, four neck flask under nitrogen atmosphere was charged with cis-(2-ethyl-6-trifluoromethyl-1,2,3,4-tetrahydro-quinolin-4-yl)arbamic acid benzyl ester (96.0 g, 254 mmol, 1.0 equiv), dry dichloromethane (720 mL), and dry pyridine (103 mL, 1.27 mol, 5.0 equiv). A solution of ethyl chloroformate (121 mL, 1.27 mol, 5.0 equiv), in dry dichloromethane (240 mL), was added slowly over 4 h. The addition was exothermic and required a reflux condenser. Once the chloroformate addition was complete, the reaction was cooled in an ice bath and 1350 mL 1N NaOH were added. The mixture was stirred 15 min, then transferred to a separatory funnel. The layers were separated and the aqueous extracted 1×1L dichloromethane. The combined dichloromethane layers were washed 1×1350 mL 1N HCl, 1×1L saturated aq. $NaHCO_3$, 1×1L brine, and dried ($Na_2SO_4$). The mixture was filtered, and the filtrate concentrated to an orange oil. 570 mL abs. ethanol were added, and the solution was concentrated. The solids were dissolved in 1370 mL abs. ethanol. 570 mL $H_2O$ were added dropwise over 45 min. The resultant thick slurry was stirred 18 h and filtered. The solids were washed with cold 7:3 abs. ethanol/water (1×250 mL, then 1×100 mL) and dried (vac oven, 45° C.) to give cis4-benzyioxycarbonylamino-2-ethyl-6-trifluoromethyl-3,4-dihydro-2H-quinoline-1-carboxylic acid ethyl ester as a white, crystalline solid (94.54 g, 83%): mp 92–96° C.; $^1$H NMR (CDCl$_3$, 400 MHz) δ0.84 (t, 3H, J=7.4 Hz), 1.28 (t, 3H, J=7.0 Hz), 1.4 (m, 2H), 1.62 (m, 1H), 2.53 (m, 1H), 4.23 (m, 2H), 4.47 (m, 1H), 4.79 (m, 1H), 5.01 (d, 1H, J=9.2 Hz), 5.18 (m, 2H), 7.4 (m, 5H), 7.5 (m, 2H), 7.57 (m, 1H); $^{13}$C NMR (CDCl$_3$, 100 MHz) δ155.97, 154.43, 139.44, 136.21, 134.33, 128.61, 128.33, 128.22, 126.32 (q, J=31.7 Hz), 126.18, 124.22, 124.19, 124.12 (q, J=273 Hz), 120.74, 120.70, 67.22, 62.24, 53.47, 46.79, 37.75, 28.25, 14.38, 9.78; DEPT spectrum: quaternary carbons δ155.97, 154.43, 139.44, 136.21, 134.33, 126.32, 124.12; CH carbons δ128.61, 128.33, 128.22, 126.18, 124.22, 124.19, 120.74, 120.70, 53.47, 46.79; CH$_2$ carbons δ67.22, 62.24, 37.75, 28.25; CH$_3$ carbons δ14.38, 9.78; IR (drifts) 3304 (s), 3067 (m), 3033 (m), 2982 (m), 2932 (m), 1723 (s), 1693 (s), 1545 (s); MS (APCI+) m/z (rel. intensity) 451 (M+H$^+$, 2), 300 (100); Anal. Calcd for C$_{23}$H$_{25}$N$_2$O$_4$F$_3$: C, 61.33; H, 5.60; N, 6.22. Found: C, 61.07; H, 5.69; N, 6.22.

Example 4 cis4-Amino-2-ethyl-6-trifluoromethyl-3.4-dihydro-2H-quinoline-1-carboxylic acid ethyl ester A one liter, four neck flask under nitrogen atmosphere was charged with cis4-benzyioxycarbonylamino-2-ethyl-6-trifluoromethyl-3,4-dihydro-2H-quinoline-1-carboxylic acid ethyl ester (40.1 g, 89 mmol, 1.0 equiv), methanol (400 mL), and ammonium formate (14.0 g, 223 mmol, 2.5 equiv). 10% Pd/C, 50% waterwet (4.0 g) was added, and the slurry heated to 40° C. over 1 h. After 1.5 h, the mixture was cooled to room temperature and filtered through celite. The cake was washed 2×100 mL methanol. The filtrate was concentrated to approximately 75 mL, transferred to a separatory funnel, and diluted with 400 mL ethyl acetate. The mixture was washed 1×125 mL saturated aq. NaHCO$_3$, 1×100 mL brine, and dried (Na$_2$SO$_4$). The mixture was filtered and the filtrate concentrated to a clear oil. The oil was crystallized from 100 mL n-heptane to give cis-4-amino-2-ethyl-6-trifluoromethyl-3,4-dihydro-2H-quinoline-1-carboxylic acid ethyl ester as a white crystalline solid (26.05 g, 93%): mp 61.5–63.50° C.; $^1$H NMR (CDCl$_3$, 400 MHz) δ0.79 (t, 3H, J=7.5 Hz), 1.24 (m, 4H), 1.42 (m, 1H), 1.51 (br s, 2H), 1.62 (m, 1H), 2.46 (m, 1H), 3.73 (m, 1H) , 4.17 (m, 2H), 4.36 (m, 1H), 7.44 (m, 2H), 7.66 (m, 1H); $^{13}$C NMR (CDCl$_3$, 100 MHz) δ154.6, 139.3, 138.9, 126.3 (q, J=32 Hz), 125.7, 124.3 (q, J=271 Hz), 123.5, 119.8, 61.96, 54.16, 46.91, 41.50, 28.85, 14.38, 9.60; DEPT spectrum: quaternary carbons δ154.6, 139.3, 138.9, 126.3, 124.3; CH carbons δ125.7, 123.5, 119.8, 54.16, 46.91; CH$_2$ carbons δ61.96, 41.50, 28.85; CH$_3$ carbons δ14.38, 9.60; IR (drifts) 3350 (s), 3293 (m), 2972 (s), 1697 (vs); MS (ES+) m/z (rel. intensity) 358 (M+H+CH$_3$CN$^+$, 55), 317 (M+H$^+$, 7), 300 (100); Anal. Calcd for C$_{15}$H$_{19}$N$_2$O$_2$F$_3$: C, 56.96; H, 6.06; N, 8.86. Found: C, 56.86; H, 6.28; N, 8.82.

Example 5

(−) (2R, 4S)-4-Amino-2-ethyl-6-trifluoromethyl-3,4dihydro-2H-quinoline-1-carboxylic acid ethyl ester hemi-(−)-dibenzoyl-L-tartrate salt A one liter flask under nitrogen atmosphere was charged with cis4-benzyloxycarbonylamino-2-ethyl-6-trifluoromethyl-3,4-dihydro-2H-quinoline-1-carboxylic acid ethyl ester (24.0 9, 75.9 mmol, 1.0 equiv) and (−) dibenzoyl-L-tartaric acid (anhydrous) (27.19 g, 75.9 mmol, 1.0 equiv). 300 mL of approximately 97% ethanol (prepared by adding 10.5 mL H$_2$O to 500 mL absolute ethanol, mixing, and measuring out 300 mL) was added. The mixture was stirred at room temperature for 18 h, then filtered. The solids were washed 1×48 mL approximately 97% ethanol, and dried to give (−) (2R, 4S)-4-amino-2-ethyl-6-trifluoromethyl-3,4-dihydro-2H-quinoline-1 -carboxylic acid ethyl ester hemi-(−)-dibenzoyl-L-tartrate salt as a white crystalline solid (14.77 g, 39%): mp 189.5–191.5 ° C. (dec); $^1$H NMR (DMSO-d6, 400 MHz) δ0.62 (t, 3H, J=7.3 Hz), 1.16 (t, 3H, J=7.1 Hz), 1.3 (m, 3H), 2.5 (m, 1), 4.1 (m, 4H), 5.63 (s, 1H, methine proton in DBTA), 7.47 (m, 2H, DBTA aromatic H's), 7.6 (m, 3H, DBTA aromatic H's), 7.68 (s, 1H), 7.95 (m, 2H), 8.2 (br s, NH$_3^+$, did not integrate); $^{13}$C NMR (DMSO-d6, 100 MHz) δ169.85, 165.53, 154.10, 140.14, 134.59, 133.51, 130.74, 129.69, 128.98, 126.74, 124.82 (q, J=31.7 Hz), 124.69 (q, J=271 Hz), 124.50, 120.90, 74.49, 62.14, 53.51, 45.94, 38.81, 28.23, 14.63, 9.58; DEPT spectrum: quaternary carbons δ169.85, 165.53, 154.10, 140.14, 134.59, 130.74, 124.82, 124.69; CH carbons δ133.51, 129.69, 128.98, 126.74, 124.50, 120.90, 74.49, 53.51, 45.94; CH$_2$ carbons δ62.14, 38.81, 28.23; CH$_3$ carbons δ14.63, 9.58; IR (drifts) 3278 (m), 2400–3100 (broad), 1703 (vs); MS (ES+) m/z (rel. intensity) 358 (M+H+CH$_3$CN$^+$, 55), 317 (M+H$^+$, 7), 300 (100); Anal. Calcd for C$_{15}$H$_{19}$N$_2$O$_2$F$_3$·C$_9$H$_7$O$_4$: C, 58.18; H, 5.29; N, 5.65. Found: C, 57.99; H, 5.15; N, 5.64; Chiral HPLC: mobile phase 950:50:2 n-hexane:2-propanol:HOAc, flow rate 1.50 mL/min, column temp 40° C., chiralpak AD 4.6×250 mm, sample concentration approximately 0.5 mg/mL in approximately 1:1 n-hexane:2-propanol. Authentic racemate shows retention times of 7.5 min and 10.0 min. (−) (2R, 4S)-4-Amino-2-ethyl-6-trifluoromethyl-3,4-dihydro-2H-quinoline-1-carboxylic acid ethyl ester hemi-(−)-dibenzoyl-L-tartrate salt: 10.0 min, 88.9%, 7.5 min <<1%, 2.0 min (solvent front) 11.1%; [α]$_D$=−153 (c=1.07, CH$_3$OH).

Example 6

(−)-(2R, 4S)-4-(3,5-Bis-trifluoromethyl-benzylamino)-2-ethyl-6-trifluoromethyl-3.4-dihydro-2H-quinoline-1-carboxylic acid ethyl ester tosylate salt (−) (2R, 4S)-4-Amino-2-ethyl-6-trifluoromethyl-3,4-dihydro-2H-quinoline-1-carboxylic acid ethyl ester hemi-(−)-dibenzoyl-L-tartrate salt (13.0 9, 26.2 mmol, 1.0 equiv) was suspended in 1,2-dichloroethane (260 mL) in a 500 mL separatory funnel. The mixture was washed 1×65 mL 1N NaOH, 1×65 mL brine, and dried (MgSO$_4$). The mixture was filtered, concentrated to approximately 80 mL, and transferred to a 250 mL three neck flask. 3,5-Bis (trifluoromethyl)benzaldehyde (4.53 mL, 27.5 mmol, 1.05 equiv) was added, and the mixture stirred 1 h at room temperature under nitrogen atmosphere. Sodium triacetoxyborohydride (11.1 g, 52.4 mmol, 2.0 equiv) was added in one portion, and the white slurry was stirred 18 h. 50 mL 1,2-dichloroethane and 50 mL 2N NaOH were added, and the aqueous layer extracted 2×50 mL 1,2-dichloroethane. The combined organic extracts were washed 1×31 mL 1N HCl, 1×50 mL saturated aq. NaHCO$_3$, 1×50 mL brine, and dried (Na$_2$SO$_4$). The mixture was filtered and concentrated to a clear oil. The oil was dissolved in methanol (71 mL). p-Toluenesulfonic acid monohydrate (5.23 g, 27.5 mmol, 1.05 equiv) was added. After 5 min, 284 mL isopropyl ether was added. The solution was concentrtated to approximately 35 mL, transferred to a 500 mL three neck flask (mech. stirrer), and diluted with 284 mL isopropyl ether. A thick white slurry formed in 10 minutes. After stirring 3 h, the slurry was filtered and the cake washed 2×70 mL isopropyl ether. After drying, (−)-(2R, 4S)-4-(3,5-bis-trifluoromethyl-benzylamino)-2-ethyl-6-trifluoromethyl-3,4-dihydro-2H-quinoline-1-carboxylic acid ethyl ester tosylate salt was isolated as a white powder (16.18 g, 86% overall): mp 191–192° C.; $^1$H NMR (DMSO-d6, 400 MHz) δ0.78 (t, 3H, J=7.5 Hz), 1.21 (t, 3H, J=7.0 Hz), 1.5 (m, 3H), 2.24 (s, 3H), 3.08 (m, 1H), 4.17 (m, 2H), 4.41 (m, 1H), 4.50 (m, 2H), 4.79 (m, 1H), 7.04 (d, 2H, J=7.9 Hz), 7.42 (d, 2H, J=7.9 Hz), 7.7 (m, 2H), 7.81 (s, 1H), 8.21 (s, 1H), 8.35 (s, 2H), 9.58 (br s, 1H), 9.83 (br s, 1 H); $^{13}$C NMR (DMSO-d6, 100 MHz) δ154.00, 145.46, 140.21, 138.39, 135.33, 132.51, 131.62, 130.79 (q, J=33.2 Hz), 128.49, 127.40, 125.82, 125.36, 124.99 (q, J=31.7 Hz), 124.59 (q, J=271 Hz), 123.69 (q, J=273 Hz), 123.44, 120.33, 62.32, 53.99, 53.79, 47.98, 33.30, 28.61, 21.13, 14.63, 9.58; DEPT spectrum: quaternary carbons δ154.00, 145.46, 140.21, 138.39, 135.33, 130.79, 124.99, 124.59, 123.69; CH carbons δ132.51, 131.62, 128.49, 127.40, 125.82, 125.36, 123.44, 120.33, 53.99, 53.79; $CH_2$ carbons δ62.32, 47.98, 33.30, 28.61; $CH_3$ carbons δ21.13, 14.63, 9.58; IR (drifts) 2300–3100 (broad), 2974 (m), 2731 (m), 2620 (m), 2455 (m), 1714 (s), 1621 (m), 1283 (vs), 1169 (vs), 1126 (vs); MS (ES+) m/z (rel. intensity) 584 (M+H+$CH_3CN^+$, 100), 543 (M+H$^+$, 80); Anal. Calcd for $C_{24}H_{23}N_2O_2F_9 \cdot C_7H_8O_3S$: C, 52.11; H, 4.37; N, 3.92. Found: C 4.22; N, 3.69; [α]$_D$=−77.9 (c =1.05, $CH_3OH$).

Example 7

(−)-(2R, 4S)-4-[(3,5-Bis-trifluoromethyl-benzyl)-methoxycarbonyl-amino]-2-ethyl-6-trifluoromethyl-3,4-dihydro-2H-quinoline-1-carboxylic acid ethyl ester mono ethanolate $Na_2CO_3$ (s) (6.75 g, 63.7 mmol, 3.5 equiv) was added to a room temperature solution of (−)-(2R, 4S)-4-(3,5-bis-trifluoromethyl-benzylamino)-2-ethyl-6-trifluoromethy-1-3,4-dihydro-2H-quinoline-1-carboxylic acid ethyl ester tosylate salt (13.0 g, 18.2 mmol, 1.0 equiv) in dry THF (130 mL). Methyl chloroformate (3.51 mL, 45.5 mmol, 2.5 equiv) was added neat, dropwise over 2 min. After 24 h, the mixture was concentrated to 65 mL, diluted with 260 mL ethyl acetate, and transferred to a separatory funnel. The mixture was washed 1×90 mL 1N HCl ($CO_2$ evolution), 1×90 mL saturated aq. $NaHCO_3$, 1×90 mL brine, and dried ($MgSO_4$). Filtration and concentration of filtrate afforded a clear oil, which was costripped 3×33 mL 2B ethanol. The oil was dissolved in 33 mL 2B ethanol and seeded with a few milligrams of (−)-(2R, 4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester mono ethanolate. After stirring 18 h at room temperature, the slurry was filtered and dried to give (−)-(2R, 4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester mono ethanolate as a white crystalline powder (8.66 g, 74%): mp 54–58° C.; $^1$H NMR ($CDCl_3$, 400 MHz, 55° C.) δ0.73 (t, 3H, J=7.0 Hz), 1.20 (t, EtOH), 1.27 (t, 3H, J=7.1 Hz), 1.42 (m, 2H), 1.66 (m, 1H), 2.25 (br s, 1H), 3.67 (q, EtOH), 3.79 (s, 3H), 4.2 (m, 3H), 4.33 (m, 1H), 5.2 (brs, 2H), 7.12 (s, 1H), 7.49 (d, 1H, J=8.3 Hz), 7.57 (d, 1H, J=8.5 Hz), 7.73 (s, 2H), 7.78 (s, 1H); $^{13}$C NMR ($CDCl_3$, 400 MHz) δ157.74, 154.37, 141.73, 140.05, 133.83, 132.14 (q, J=33 Hz), 126.94, 124.49, 123.96 (q, J=273 Hz), 123.13 (q, J=273 Hz), 121.31, 119.17, 62.29, 58.28, 54.42, 53.71, 53.08, 46.67, 37.01, 29.02, 18.29, 14.32, 9.22, (note: the fourth quartet appears to be buried under the δ126.94 peak, with J approximately 32 Hz); DEPT spectrum: quaternary carbons δ157.74, 154.37, 141.73, 140.05, 133.83, 132.14, 123.96, 123.13; CH carbons δ126.94, 124.49, 121.31, 119.17, 54.42, 53.08; $CH_2$ carbons δ62.29, 58.28, 46.67, 37.01, 29.02; $CH_3$ carbons δ53.71, 18.29, 14.32, 9.22; IR (drifts) 3489 (s), 2974 (s), 2884 (m), 1701 (vs), 1280 (vs), 1131 (vs); MS (ES+) m/z (rel. intensity) 601 (M+H$^+$, 100); Anal. Calcd for $C_{26}H_{25}N_2O_4F_9 \cdot C_2H_6O$: C, 52.01; H, 4.83; N, 4.33. Found: C, 51.84; H, 4.54; N, 4.33; chiral HPLC: mobile phase 950:50:2 n-hexane:2-propanol:HOAc, flow rate 1.0 mL/min, 254 nm, chiralpak AD 4.6×250 mm, column temp 40° C., sample concentration approximately 0.5 mg/mL in 90:10 n-hexane:2-propanol, authentic racemate retention times 3.6 and 4.6 min. (−)-(2R, 4S)-4-[(3,5-Bis-trifluoromethyl-benzyl)-methoxycarbonyl-amino]-2-ethyl-6-trifluoromethyl-3,4-dihydro-2H-quinoline-1-carboxylic acid ethyl ester mono ethanolate shows 4.6 min, 99.1% and 3.6 min, not detected; [α]$_D$=−93.3 (c =1.08, $CH_3OH$).

Example 8

Anhydrous, (−)-(2R,4S)-4-[(3.5-Bis-trifluoromethyl-benzyl)-methoxycarbonyl-amino]-2-ethyl-6-trifluoromethyl-3,4-dihydro-2H-quinoline-1-carboxylic acid ethyl ester A 2.6 gram portion of (−)-(2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (a mixture of predominantly amorphous material with traces of ethanolate crystalline form; the title compound was also prepared in an analogous manner starting from pure amorphous or pure ethanolate material) was charged to 13 milliliters of hexanes and heated to effect a solution at about 60° C. The heat was removed and the reaction was allowed to cool to ambient over a one hour period. The reaction was seeded with anhydrous (−)-(2R, 4S)-4-[(3,5-bis-trifluoromethyl-benzyl)-methoxycarbonyl-amino]-2-ethyl6-trifluoromethyl-3,4-dihydro-2H-quinoline-1 -carboxylic acid ethyl ester and granulated for eighteen hours under ambient conditions. Alternatively, the anhydrous crystals may be prepared from hexanes without seeding. The product was collected by filtration and air dried.

Fusion Microscopy: In Type A oil - - - dissolution at 50° C.
  Dry - - - clear melt at 86° C.
Appearance: Free flowing white powder.

Example 9

Monoethanolate, (−)-(2R,4S)-4-[(3,5-Bis-trifluoromethyl-benzyl)-methoxvcarbonyl -amino]-2-ethyl-6-trifluoromethyl-3,4-dihydro-2H-quinoline-1-carboxylic acid ethyl ester 4.0 grams of (−)-(2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester were dissolved in 3.5 ml ethanol and sonicated for two minutes to complete dissolution. A white solid formed to which 10 ml ethanol was added and stirred at ambient temperature overnight. A white powder was filtered and collected on 0.22 μm LS filter paper followed by washing with about 15 ml. Ethanol.

Fusion Microscopy: In Type A oil - - - melt and dissolution at 43° C. with loss of water
  Dry - - - clear melt at 43° C.
Appearance: free-flowing white power.

Example 10 cis4-[(3,5-Bis-trifluoromethyl-benzyl)-methoxycarbonyl-amino]-2-ethyl-6-trifluoromethyl-3,4-dihydro-2H-quinoline-1-carboxylic acid ethyl ester A solution of cis4-(3,5-bis-trifluoromethyl-benzylamino)-2-ethyl-6-trifluoromethy1-3,4-dihydro-2H-quinoline-1- carboxylic acid ethyl ester (2.0 g, 3.7 mmol) and pyridine (0.58 g, 7.4 mmol) in 100 mL of dichloromethane was cooled in an icewater bath as methyl chlorofomate (0.87 g, 9.2 mmol) was added slowly. After stirring overnight at room temperature, the reaction mixture was washed twice with a 2N hydrochloric acid solution, dried over magnesium sulfate, filtered and concentrated in vacuo to afford the crude product, which was purified by silica gel chromatography using 5–10% ethyl acetate/hexanes as eluent to afford 1.8 g of the title product. MS m/z 601 (M$^+$+1); $^1$H NMR (coalescing mixture of conformers, CDCl$_3$) δ0.6–0.8 (bm, 3H), 1.2–1.3 (bm, 3H), 1.3–1.5 (bm, 2H), 1.6–1.75 (bm, 1H), 2.1–2.3 (bm, 1H), 3.7–3.9 (bs, 3H), 4.0–4.4 (bm, 4H), 5.0–5.6 (bm, 2H), 7.1 (s, 1H), 7.4–7.6 (bm, 2H), 7.6–7.8 (bm, 3H). [2R,4S]-4-[(3,5-bis-trifluoromethyl-benzyl)-methoxycarbonyl-amino]-2-ethyl -trifluoromethyl-3,4-dihydro-2H-quinoline-1-carboxylic acid ethyl ester was prepared in optically enriched form by resolution of the corresponding racemate, or an intermediate in its synthesis, using standard methods.

Example 11

Anhydrous (−)-(2R,4S)-4-[(3,5-bis-trifluromethylbenzyl)-methoxycarbonyl-amino]-2-ethyl-6-trifluoromethyl-3,4-dihydro-2H-quinoline-1-carboxylic acid ethyl ester A crude solution of approximately 42 g of (−)-(2R,4S)-4-[(3,5-bis-trifluoromethylbenzyl) -methoxycarbonyl-amino]-2-ethyl4 -trifluoromethyl-3,4-dihydro-2H-quinoline-1-carboxylic acid ethyl ester in 500 ml of ethyl acetate (obtained via the process described in Example 7) was concentrated under vacuum to a volume of 100–135 ml. The remaining ethyl acetate was displaced with 3×220 ml 2B EtOH to a final volume of 100–135 ml. This solution was seeded with a crystal of anhydrous (−)-(2R,4S)-4-[(3,5-bis-trifluromethylbenzyl)-methoxycarbonyl-amino]-2-ethyl-6tifluoromethy1-3,4-dihydro-2H-quinoline-1-carboxylic acid ethyl ester. After stirring 18 hr at room temperature the slurry was filtered and vacuum dried to give 19.81 g of anhydrous (−)-(2R,4S)-4-[(3,5-bis-trifluoromethylbenzyl)-methoxycarbonyl-amino]-2-ethyl-6-trifluoromethyl-3,4-dihydro-2H-quinoline-1-carboxylic acid ethyl ester. The melting point behaviour was the same as the material prepared via Example 8 confirming the anhydrous nature of the material.

What is claimed is:

1. The stereoisomer (−)-(2R,4S )-4-(3,5-bis-trifluoromethylbenzylamino)-2-ethyl-6-trifluoromethyl-3,4-dihydro-2H-quinoline-1-carboxyl acid ethyl ester or salts thereof.

2. The stereoisomer as recited in claim 1 wherein the salt is the 4-toluene-sulfonate.

3. The (−)di-p-toluoyl-L-tartaric acid salt of cis-4-amino-2-ethyl6-trifluoromethyl-3,4-dihydro-2H-quinoline-1-carboxylic acid ethyl ester.

4. The (−)di-benzoyl-L-tartrate salt of cis-4-amino-2-ethyl-6-trifluoromethyl-3,4-dihydro-2H-quinoline-1-carboxylic acid ethyl ester.

5. (−)(2R,4S)-4-Amino-2-ethyl-6-trifluoromethyl-3,4-dihydro-2H-quinoline-1-carboxylic acid ethyl ester or salts thereof.

6. The stereoisomer as recited in claim 5 wherein the salt is the (−)di-benzoyl-L-tartrate salt.

7. The stereoisomer as recited in claim 5 wherein the salt is the (−)di-p-toluoyl-L-tartaric acid salt.

8. A process for preparing (−)-(2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprising combining (−)-(2R,4S)-4-(3,5-bis-trifluoromethyl-benzylamino)-2-ethyl-6-trifluoromethyl-3,4-dihydro-2H-quinoline-1-carboxylic acid ethyl ester, tosylate salt, sodium carbonate and methyl chloroformate in tetrahydrofuran at a temperature of about 20° C. to about 25° C.

9. A process for preparing (−)-(2R,4S)-4-(3,5-bis-triluoromethyl-benzylamino)-2-ethyl-6-trifluoromethyl-3,4-dihydro-2H-quinoline-1-carboxylic acid ethyl ester, 4-toluene-sulfonate comprising
  a. combining 4-amino-2-ethyl-6-trifluoromethyl-3,4-dihydro-2H-quinoline-1-carboxylic acid ethyl ester and (−) dibenzoyl-L-tartaric acid or ((−)di-p-toluoyl-L-tartaric acid to form the (−) dibenzoyi-L-tartaric acid salt or di-p-toluoyl-L-tartaric acid salt thereof;
  b. combining the resulting salt, 1,2-dichloroethane and an aqueous base with 3,5-bis(trifluoromethyl) benzaldehyde, followed by the addition of sodium triacetoxyborohydride; and
  c. adding 4-toluene sulfonic acid monohydrate.

10. The process as recited in claim 9 wherein 4-amino-2-ethyl-6-trifluoromethyl-3,4-dihydro-2H-quinoline-1-carboxylic acid ethyl ester and (−) dibenzoyl-L-tartaric acid (anhydrous) are combined.

11. A process for preparing cis-4-amino-2-ethyl-6-trifluoromethyl-3,4-dihydro-2H-quinoline-1-carboxylic acid ethyl ester comprising combining cis-4-benzyoxycarbonylamino-2-ethyl-6-trifluoromethyl-3,4-dihydro-2H-quinoline-1-carboxylic acid ethyl ester and ammonium formate in methanol with palladium/carbon to form a slurry and heating the resulting slurry at a temperature of about 35° C. to about 60° C. for about 30 minutes to about 3 hours.

12. A process for preparing cis-(2-ethyl-6-trifluoromethyl-1,2,3,4-tetrahydro-quinolin-4-yl)-carbamic acid-R$^1$-ester wherein R$^1$ is benzyl,t-butyl or (C$_1$–C$_4$)alkyl comprising: combining vinyl-carbamic acid-R$^1$, (1-benzotriazol-1-yl-propyl)-(4-trifluoromethyl-phenyl)-amine and 4-toluene-sulfonic acid monohydrate in toluene at a temperature of about 50° C. to about 90° C.

13. The process as recited in claim 12 with the additional step of combining the resulting cis-(2-ethyl-6-trifluoromethyl-1,2,3,4-tetrahydro-quinolin4-yl)-carbamic acid-R$^1$-ester with pyridine and ethyl chloroformate in dichloromethane in to prepare cis-4-R$^1$-oxycarbonylamino-2-ethyl-6-trifluoromethyl-3,4-dihydro-2H-quinoline-1-carboxylic acid ethyl ester.

14. A process for preparing (−)-(2R,4S)-4-[(3,5-bis-trifluoromethyl-benzyl)-methoxycarbonyl-amino]-2-ethyl-6trifluoromethyl-3,4-dihydro-2H-quinoline-1-carboxylic acid ethyl ester comprising
  a. combining vinyl-carbamic acid-R$^1$, wherein R$^1$ is benzyl, (1-benzotriazol-1-yl-propyl)-(4-trifluoromethyl-phenyl)-amine and 4-toluene-sulfonic acid monohydrate in toluene at a temperature of about 50° C. to about 90° C. to prepare cis-(2-ethyl-6-trifluoromethyl-1,2,3,4-tetrahydro-quinolin4-yl)-carbamic acid-R$^1$-ester wherein R$^1$ is benzyl;
  b. combining the resulting cis-(2-ethyl-6-trifluoromethyl-1,2,3,4-tetrahydro-quinoline-4-yl)-carbamic acid-R$^1$-ester with pyridine and ethyl chloroformate in dichloromethane to prepare cis4-R$^1$-oxycarbonylamino-2-ethyl-6-trifluoromethyl-3,4-dihydro-2H-quinoline-1-carboxylic acid ethyl ester;
  c. combining cis4-R$^1$oxycarbonylamino-2-ethyl-6-trifluoromethyl-3,4-dihydro-2H-quinoline-1- carboxylic acid ethyl ester and ammonium formate in methanol with palladiumicarbon to form a slurry and heating the resulting slurry at a temperature of about 35° C. to about 60° C. for about 30 minutes to about 3 hours to prepare 4-amino-2-ethyl-6-trifluoromethyl-3, 4-dihydro-2H-quinoline-1-carboxylic acid ethyl ester;

d. combining 4-amino-2-ethyl-6-trifluoromethyl-3,4-dihydro-2H-quinoline-1-carboxylic acid ethyl ester and (−)dibenzoyl-L-tartaric acid or (−)di-p-toluoyl-L-tartaric acid to form the (−)dibenzoyl-L-tartaric acid salt or (−)di-p-toluoyl-L-tartaric acid salt thereof;

e. combining the resulting salt, 1,2-dichloroethane and an aqueous base with 3,5-bis(trifluoromethyl) benzaldehyde, followed by the addition of sodium triacetoxyborohydride to form a product;

f. combining said product and 4-toluene sulfonic acid monohydrate to prepare (−)-(2R,4S)-4-(3,5-bis-trifluoromethyl-benzylamino)-2-ethyl-6-trifluoromethyl-3,4-dihydro-2H-quinoline-1-carboxylic acid ethyl ester, 4-toluene-sulfonate; and g. combining (−)-(2R,4S)-4-(3,5-bis-trifluoromethyl-benzylamino)-2-ethyl-6-trifluoromethyl-3,4dihydro-2H-quinoline-1-carboxylic acid ethyl ester, tosylate salt, sodium carbonate and methyl chloroformate in tetrahydrofuran at a temperature of about 20° C. to about 25° C.

15. An anhydrous crystalline form of (−)-(2R,4S)-4-3,5-bistrifluoromethylbenzylamino)-2-ethyl-6-trifluoromethyl-3,4-dihydro-2H-quinoline-1-carboxyl acid ethyl ester.

16. An ethanolate crystalline form of (−)-(2R,4S)-4-3,5-bistrifluoromethylbenzylamino)-2-ethyl-6-trifluoromethyl-3,4-dihydro-2H-quinoline-1-carboxyl acid ethyl ester.

17. A method for treating atherosclerosis, peripheral vascular disease, dyslipidemia, hyperbetalipoproteinemia, hypoalphalipoproteinemia, hypercholesterolemia, hypertriglycridemia, familalhypercholesterolemia, cardiovascular disorders, angina, ischemia, cardiac ischemia, stroke, myocardial infarction, reperfusion injury, angioplastic restenosis, hupertension, vascular complications of diabetes, obesity or endotoxemia in a mammal in need thereof comprising administering to said mammal an effective dose of an anhydrous or ethanolate crystalline form of (−)-(2R,4S)-4-3,5bistrifluoromethylbenzylamino)-2-ethyl-6-trifluoromethyl-3,4-dihydro-2H-quinoline-1-carboxyl acid ethyl ester.

18. The method of claim 17 wherein said anhydrous or ethanolate crystalline form of (−)-(2R,4S)-4-3,5-bistrifluoromethylbenzylamino)-2-ethyl-6-trifluoromethyl-3,4-dihydro-2H-quinoline-1-carboxyl acid ethyl ester is administered in combination with a second compound selected from the group consisting of a HMG-CoA reductase inhibitor, a microsomal triglyceride transfere protein/Apo B secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor and a bile acid sequestrant.

* * * * *